(12) United States Patent
Rodilla Sala et al.

(10) Patent No.: US 8,894,718 B2
(45) Date of Patent: Nov. 25, 2014

(54) SYSTEM FOR REMOTE MANAGEMENT IN AMBIENT INTELLIGENCE ENVIRONMENTS USING ELECTROMYOGRAPHIC SIGNALS

(76) Inventors: Vicente Rodilla Sala, Puzol (ES); Manuel De Entrambasaguas Barretto, Valencia (ES); Juan Manuel Belda, Valencia (ES); Antonio Reig Fabado, Valencia (ES); Antonio Miranda, Valenica (ES)

( * ) Notice: Subject to any disclaimer, the term of this patent is extended or adjusted under 35 U.S.C. 154(b) by 962 days.

(21) Appl. No.: 12/745,244

(22) PCT Filed: Nov. 26, 2008

(86) PCT No.: PCT/ES2008/070214
§ 371 (c)(1),
(2), (4) Date: Jul. 12, 2010

(87) PCT Pub. No.: WO2009/068720
PCT Pub. Date: Jun. 4, 2009

(65) Prior Publication Data
US 2010/0305467 A1    Dec. 2, 2010

(30) Foreign Application Priority Data

Nov. 27, 2007  (ES) .................................. 200703149

(51) Int. Cl.
| | |
|---|---|
| *A61F 2/70* | (2006.01) |
| *A61B 5/04* | (2006.01) |
| *A61B 5/0488* | (2006.01) |
| *A61B 5/00* | (2006.01) |
| *G06F 3/01* | (2006.01) |
| *A61B 5/11* | (2006.01) |

(52) U.S. Cl.
CPC .............. *G06F 3/015* (2013.01); *A61B 5/0488* (2013.01); *A61B 5/0002* (2013.01); *A61B 5/11* (2013.01)
USPC .............. 623/25; 600/544; 600/545; 600/546

(58) Field of Classification Search
USPC .............................. 600/546, 544, 545; 623/25
See application file for complete search history.

(56) References Cited

U.S. PATENT DOCUMENTS 6,334,068 B1 *  12/2001  Hacker ......................... 600/545
6,859,663 B2 *   2/2005  Kajitani et al. ............... 600/546

(Continued)

FOREIGN PATENT DOCUMENTS

| | | |
|---|---|---|
| DE | 202006008616 U1 | 9/2006 |
| EP | 1308826 A1 | 5/2003 |
| WO | WO9828678 A | 7/1998 |

OTHER PUBLICATIONS

A Novel EMG-based Human-Computer Interface for Persons with Disability, Inhyuk Moon, Myoungjoon Lee, and Museong Mun, Korea Orthopedics & Rehabilitation Engineering Center (KOREC), Incheon, Korea, IEEE, 2004.*

(Continued)

*Primary Examiner* — Sean Dougherty
(74) *Attorney, Agent, or Firm* — Albert Bordas, P.A.

(57) ABSTRACT

The system is comprised of an interface (1) consisting of one or more electrodes capturing electromyographic (biolectric muscle activity) signals, an earphone/microphone and a radiofrequency transmitter/receiver; a nexus module (2), with means for the encoding and interpretation of the electromyographic signals which taking into account both their duration as well as their amplitude and time lapse interval, wirelessly connected to the transmitter/receiver of the interface (1); and a controller (3), consisting of means for controlling and managing the devices comprising the ambient intelligence environment of a domotic, inmotic, military or other types, the input of which is connected to the output of the nexus module (2).
Additionally, the communication facilitated by the earphone/microphone is completed with glasses incorporating a device capable of projecting visual messages on the inner side thereof.

3 Claims, 1 Drawing Sheet

(56) References Cited

U.S. PATENT DOCUMENTS

| | | |
|---|---|---|
| 6,941,171 B2 * | 9/2005 | Mann et al. .................. 607/39 |
| 7,359,081 B2 * | 4/2008 | Wanda et al. ................ 358/1.15 |
| 8,311,623 B2 * | 11/2012 | Sanger ........................ 600/546 |
| 2006/0004298 A1 | 1/2006 | Kennedy et al. |
| 2006/0209343 A1 * | 9/2006 | Wanda et al. ................ 358/1.15 |
| 2007/0276281 A1 * | 11/2007 | Sarkela ....................... 600/546 |
| 2008/0200827 A1 * | 8/2008 | Cyphery et al. ............. 600/546 |
| 2008/0228240 A1 * | 9/2008 | Edell et al. ................... 607/48 |
| 2010/0030096 A1 * | 2/2010 | Bradley et al. .............. 600/544 |
| 2010/0292606 A1 * | 11/2010 | Prakash et al. .............. 600/554 |
| 2010/0305467 A1 * | 12/2010 | Rodilla Sala et al. ........ 600/546 |

OTHER PUBLICATIONS

Microprocessor Based Algorithms for Controlling Electromyogram-Driven Devices, Nikola Mrvaljevic, Ryan Zaczynski, Eugene Chabot, Ying Sun, PhD, Department of Electrical, Computer and Biomedical Engineering, IEEE 2007.*

International Search Report, mailing date Apr. 3, 2009, for corresponding International Application No. PCT/ES2008/070214.

* cited by examiner

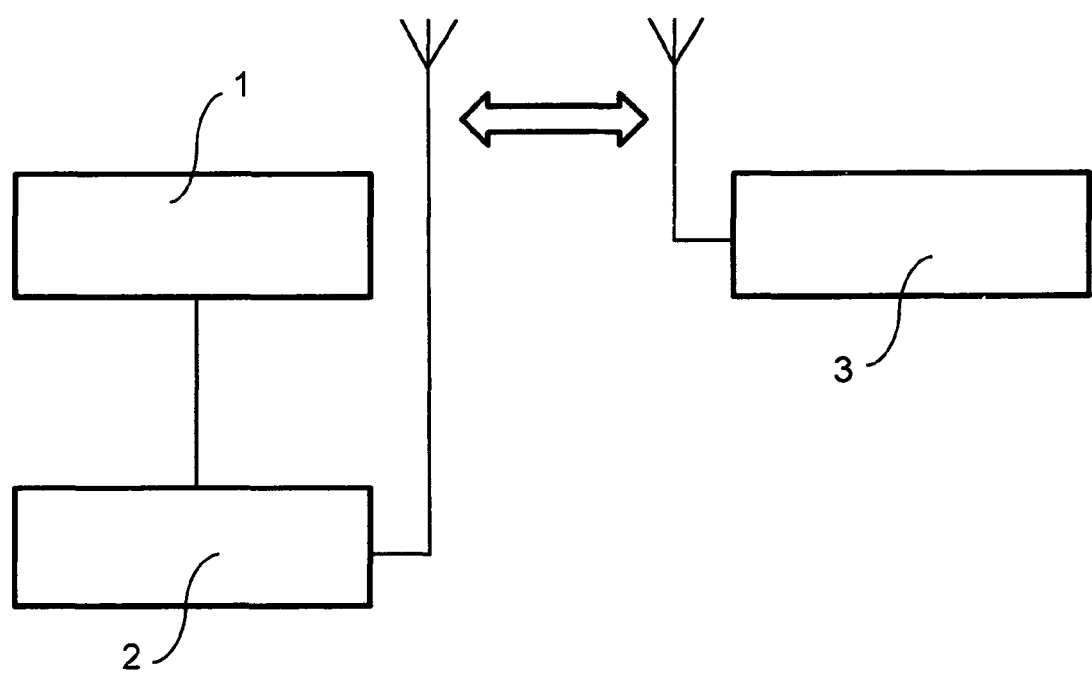

SYSTEM FOR REMOTE MANAGEMENT IN AMBIENT INTELLIGENCE ENVIRONMENTS USING ELECTROMYOGRAPHIC SIGNALS

This invention relates to a system for interacting remotely with an intelligent environment, both in the home (domotic environment) and in buildings for tertiary and industrial use, including industrial buildings (inmotic environment) or other environments, by means of the use of electromyographic signals generated voluntarily by the user.

The invention falls within the framework of the Physiological Computing field, which consists of using physiological signals as an input interface to ICT (Information and Communication Technology) systems, but also to any device requiring the user's commands for its functioning or use. The objective is to convert the nervous system's bioelectrical signals into inputs into a computer in real time to enrich interactivity. The interface of the invention accomplishes new goals, given that it functions like a remote control unit located within the user's own body.

BACKGROUND OF THE INVENTION

In domotic/inmotic environments, in driving or in playing sports, devices are known which function by means of switches or keypads or rather by means of remote control units, by cable or wirelessly (infrareds, radio frequency, bluetooth or voice-controlled technologies). However, in most cases, they must be manipulated using one's hands. This poses a major problem in situations in which users need their hands for the activity they are carrying out, such as, for example, driving, playing some sports (sailing, diving, skiing) or on security missions (military, police).

Other times, for example, in the voice-controlled systems, their usefulness is conditioned to certain environments in which there are not interferences due to background noise or rather when, for security-related reasons, it is not possible to use one's voice.

In addition to the above, the systems described hereinabove sometimes pose privacy-related problems in public environments in which users may be watched by third parties under conditions which do not ensure their privacy, for example at ATM machines or during the holding of meetings, events and ceremonies.

Lastly, people with physical disabilities which hinder or make it impossible for them to use their hands would benefit from a management device such as the one proposed, in the domotic and other realms.

To solve the problems described hereinabove, the use of physiological signals voluntarily modified by the users has been set out in theory. Thus, the field of Physiological Computing has researched the use of different physiological signals as possible inputs, for example, a personal computer, the most outstanding signals of which are the electrooculographic, electroencephalographic and electromyographic signals.

The electrooculogram (EOG) measures the differential in potential between the cornea and retina of the eye, a circumstance affording the possibility of recording the speed and direction of eye movement by means of electrodes placed on the skin in the vicinity of the eye. The electrode nearest to the cornea will record a positive potential, the one nearest the retina recording a negative potential. On moving one's eyes, the cornea and retina positions change in relation to the electrode, which gives rise to a change in potential. The EOG signal can be used by persons who have a high degree of disability, nevertheless, the EOG-based systems are comparatively expensive, requiring a great deal of attention and effort to control the proper cursor, and both calibrating and learning how to use them are complex.

The electroencephalogram (EEG) measures the brain's bioelectrical activity, and its use as an interface depends upon each user's ability to learn to control it. The physiological rhythms of the EEG in healthy adults when awake are alpha (8-13 Hz) and beta (above 13 Hz), although there may also be some theta (4.7 Hz) activities. These rhythms are of differing topographic distribution, are reactive to certain stimuli and are related to different states of alertness. With proper training, it is possible to generate EEG patterns which can be used, for example, to control the movements of a cursor or select letters or words on the computer screen. The main drawbacks of the EEG signal as an interface are their limitation in the band width and their spatial resolution, in addition to detection faults, contamination by electromyography and the effect of psychological variables. In general, the capacity to modulate the frequency of the brain's bioelectrical activity requires a great deal of training, for example, persons who have practice in meditating.

Electromyography (EMG) is based on measuring the bioelectrical activity associated with voluntary muscle contraction. One of the advantages of this signal is its relative immunity to the interferences coming from other physiological signals, in comparison to the EOG and EEG signals. The EMG signal can be used in different ways to manage a system, for example, in a way similar to a switch (ON/OFF system) but turning on/off a certain action with a voluntary muscle contraction. Another theoretical possibility would be the use of different estimated magnitudes of the EMG, which would make a proportional type of management possible. Lastly, it is feasible to define a pulse code in order to be able to perform different actions with one same muscle. This last strategy has been used, for example, in bioelectrical prosthesis control and is based on a 3-bit code (high-amplitude signal, low-amplitude signal and no contraction) without it being possible for a given code to start with "no contraction", which makes a maximum of 18 commands possible. This system does not define a language based on the structure of the signal recorded.

In the state of the art, systems are currently known which employ this type of physiological signals as a computer input, one of which is a commercial product called Cyberlink-Brainfingers. This is a hardware (Cyberlink) and software (Brainfingers) system making it possible to control a computer (mouse/cursor, keyboard/keys) without using one's hands. It uses three types of neurophysiological signals: EEG, EOG and EMG. It is comprised of four elements: headband, with three plastic sensors for each one of the three signals, interface box (filter, amplifier, A/D converter) with USB port for connecting to the computer, cables and software which the user must install on the computer. The system picks up the three types of signals and distributes them among 11 information channels called brainfingers. Besides these 11 channels, Brainfingers combines the signals of the EEG and EMG channels into one single channel called BrainBody, which also serves to help users to modify their EEG activity by means of feedback from their EMG activity (on decreasing the degree of muscle contraction, users learn to relax and facilitate the start of the alpha rhythm). In users with limited facial mobility, the software can be formatted so that EOG or BrainBody will replace the EMG input.

In this system, the equivalent of a click of the mouse is a short contraction, the double click being two contractions. A sustained contraction (called "long click") activates the cursor speed switch, which switches from "high speed and low resolution" to "low speed and high resolution" in order to be able to more easily click on icons or small targets on the computer screen. The system recognized up to four types of clicks depending on their duration (0.3, 0.6, 0.98 and 1.2 ms).

This system is explicitly for persons with a severe motor disability of neurological origins: cerebral palsy, amiotrophic lateral sclerosis, muscular dystrophy, multiple sclerosis, spinal cord injuries and patients with craneoencephalic trama sequelae.

Brainfingers has the following limitations:

1) Signal Type:

Brainfingers simultaneously uses the three neurophysiological signals described hereinabove. It gives the EMG channel a greater number of and more complex functions than the other two signals, which corresponds to the aforementioned EOG and EEG limitations as interfaces. Given that it is for users who have a major motor disability (EMG), it attempts to make up for this deficit with the user's EOG and EEG activity.

2) EMG Signal Characteristics

Muscle used: Brainfingers does not distinguish the action of an individual muscle, given that it picks up the EMG activity from the area beside the eyebrow, and therefore from both the frontalis and temporalis muscles.

Electrodes: Brainfingers places its electrode to pick up surface EMG on a fabric band around the forehead.

Parameters: Brainfingers uses only the SEMG signal duration parameter, and its code is limited to the mouse click, presented as a single click (of four different durations), double click and long click.

3) User:

Brainfingers is specifically for people who have a severe motor disability of neurological origins who have residual motor activity of the frontalis or temporalis muscle.

4) Objective:

Brainfingers is designed specifically so that a user with a severe motor disability may communicate with a computer and with other people through the computer, as well as for providing moments of entertainment to someone who, under these conditions, is constantly lying in the same position by means of educational games, video games and musical composition.

5) Way of Use:

Brainfingers connects the user to the computer by means of cables and interacts with the user exclusively by way of the computer screen.

One of the objectives of the present invention is to control the environment using exclusively the EMG signal.

A further objective of the present invention is to make it possible to record the EMG signal from the skin surface or beneath the skin surface (i.e. from a piercing).

A further objective of the present invention is to use a specific muscle to facilitate the use of the system and enhance discreetness and ergonomics.

A further objective of the present invention is to make it possible to use several alternative muscles, enabling the users to choose the one which they find to be best and to rotate using one and another so as to avoid fatigue and overstrain.

A further objective of the present invention is for it to be possible for it to be used by persons who have enough motor control over any facial or cranial muscle and by any user with a motor disability.

A further objective of the present invention is to broaden the scope of application to make it possible for users to interrelate with their environment.

A further objective of the present invention is to broaden the scope of interaction by developing an alternative to the wired connection.

Yet a further objective of the present invention is the development of a language based on the parameters of duration, amplitude and interval of the EMG signal.

DESCRIPTION OF THE INVENTION

The new interface proposed in the present invention mainly communicates with the users by audio, which makes it usable anywhere, given that it does not force users to be looking at a fixed screen. Additionally, it also makes communication possible by way of images or visual messages projected into glasses the users wear, which are connected to the system. Regarding the former technique, the invention takes into account the EMG signal amplitude and interval parameters, which makes it possible to have the elements necessary for developing a myogenic language, as is described in following, thus making it possible to express a greater number of commands.

The system of the invention comprises an interface which possesses at least one electrode in contact with the user's body and which is integrated into or connected, in turn, to a nexus module through which it communicates, by radio frequency, with the programmable controller (or equivalent system) of a domotic/inmotic type of environment. The system enables the user proper to interrelate remotely with the aforementioned intelligent environment. We shall term this new biological telemanagement utility "Telebionics".

The invention is supported on the development of techniques for utilizing electromyographic signals for their widespread application in the interaction with intelligent environments. The environment is referred to as "intelligent" because it takes in the postulates of Ambient Intelligence, a vision of the near future in which the environment is capable of detecting the user presence by responding to their needs, facilitating both performing tasks and user-environment communications. In domotics and inmotics, the user's interaction with the environment is currently by way of physical interfaces (keyboards, screens, remote control units). This new system eliminates them all, on integrating the interface into the user's own body.

Electromyography (EMG) is the recording of the bioelectrical activity of muscles. This electrical activity is generation in the muscle fibers as a result of the voluntary activation of the motor pathways, giving rise to the physical phenomenon of muscle contraction. In this interface, the EMG recording is done by means of electrodes placed on the skin surface over the muscle, although the recording may also be subcutaneous or intramuscular. The EMG signal, once processed, is the interface input element, whilst the nexus module is the output element. By means of a controller, this module puts the user in touch with the intelligent environment by means of a programmable receiver-actuator (or another system equivalent to an automaton) in charge of performing tasks in said environment.

The system makes it possible to perform any task assigned to the commands given by the user in the aforementioned intelligent environment. These commands are based on the development of a new communications standard, called Myogenic Language, which the present invention also provides; a code based on the voluntary myogenic activity, defined as the muscle contraction made by the user for the purpose of communicating with the intelligent environment. The Myogenic Language used in the present invention is based on three parameters. The first two are the amplitude (A) and the duration (D) of the EMG signal. The amplitude may be small (S) or large (L), and the duration, short (S) or long (L). The combination of these variables gives rise to the four basic letters of the Myogenic Language proposed: AS/DS, AS/DL, AL/DS and AL/DL. The third parameter is the time lapse interval between the generation of one myogenic letter and the next. Thus, the Myogenic language possesses a vocabulary with a sufficient number or simple, clear, specific commands to manage the environment. The muscles from which the EMG signals are triggered are hence termed. "trigger muscles" and require the integrity of the motor system which controls them. They may be superficial, preferably discreet and easy to modulate in their contraction. The facial muscles or others in the cranial region meet these requirements for a large number of users, including those with spinal cord injuries, who are therefore ideal candidates, although the system can also function from other muscle groups.

The advantage the device of the invention provides are as follows:

1) Hands-free. The system leaves the user's hands free and does not require those users whose manual functions are impaired to use their hands.
2) No remote control unit needed. The "remote control" unit ceases to be an external unit to be integrated into the user, in close contact with their bodies and with an ergonomic (not uncomfortable) and discreet (unnoticeable) design. Conventional remote control units then become obsolete.
3) Self-dependence and Mobility. Users need not be in front of a screen to select tasks and give commands, given that the system communicates with them anywhere in the home, building, industrial environment, vehicle, watercraft, etc. completely ergonomically.
4) Discreteness. Users can perform different tasks without those around them knowing what tasks they are performing. This provides greater privacy in all the commands or actions.
5) Versatility. The system makes it possible to perform any task subject to being linked to a domotic, inmotic or other environment (PLCs, etc.). For example, any of the customary tasks in the automation of the home, such as temperature and humidity control, electric and natural lighting, audio and video entertainment systems, security, communications, door control or household robotics systems. At the inmotic level, the switching function, motor operation, frequency variators, etc.
6) Safety. The system increases user safety in the event of emergency, given that it can notify this situation when and where it happens without any need of moving to issue this alert.

BRIEF DESCRIPTION OF THE DRAWINGS

FIG. 1 provides the block diagram of the system of the invention.

DETAILED DESCRIPTION OF A PREFERRED EMBODIMENT

In one preferred embodiment, the system of the invention comprises three physical elements. The interface (1) plus the nexus module (2), which users wear on their bodies, connected to a controller (3) which performs the tasks in the environment to be controlled. The interface (1)—nexus module (2) assembly has a transmitter-receiver by radio frequency or another two-way wireless type, as shown in the block diagram in FIG. 1.

The interface (1) comprises at least one myogenic signal-capturing electrode and means for the encoding and interpretation thereof, an earphone/microphone, and can incorporate a micro-projector of images, graphics, icons or texts.

The nexus module (2) is an electronic device, the input of which is connected to the interface (1) the user employs, and the output of which is connected, by means of a radiofrequency or other type of wireless transmitter/receiver, to a controller (3) comprised of one or more automatons equipped with a high-level programming logic, or rather simple contactor-relays. Thus, all types of maneuvers can be performed on household appliances (including thermostats), apparatuses (including mobile or fixed telecommunications) and even control of machinery for production or provision of services. The system is also provided visually-disabled persons or those with limited mobility with high-level management capacity (in its audio feedback modality), tremendously increasing their safety and comfort.

The system functions as follows:

1. Enabling. The interface (1), the nexus module (2) and the controller (3) must be turned on and operative.
2. User recognition. By means of the Myogenic Language, the users personalize and display their user code. Commands are generated by means of the Myogenic Language.
3. System welcome message and display of the task menu. The nexus module (2) emits this message and transmits it to the interface (1). The communication reaches the user auditively (by means of an earphone/microphone incorporated into the interface), as well as visually (by means of icons, text or images projected from the interface onto glasses connected to the system) or others.
4. Command generation. The commands are given by means of the Myogenic Language. The electrode of the interface (1) picks up the voluntary myogenic activity made with the trigger muscles.
5. EMG signal processing. The interface (1) and the nexus module (2) incorporate the electronic elements necessary to convert the voluntary myogenic activity into an electrical signal making it possible to transmit the same remotely.
6. Command transmission. The EMG signals are transmitted wirelessly to the controller (3).
7. Performance of commands. The controller (3) of the intelligent environment performs the task assigned to the command requested.
8. Confirmation of the command having been performed and information on the system status. The nexus module (2) receives from the controller (3) the confirmation of the completion of the task performed, as well as notifications concerning any incident or variations in the system. This information is transmitted from the nexus module (2) to the user by way of the interface (1) by means of auditory or visual messages.

Before using the system, the user must learn to master the Myogenic Language. The interface (1), by means of a tutorial, helps the user to calibrate their voluntary myogenic activity for effectively carrying out a muscle contraction of greater or lesser amplitude (intensity of the contraction) and duration (of said contraction), so that the user can learn and be capable of reproducing the specific commands of the myogenic language. This learning process is carried out by auditory feedback by means of the conversion of the EMG signal into an acoustic signal received by means of the earphone/microphone of the interface (greater amplitude of the EMG signal=louder sound, longer duration of the EMG signal=long duration of the sound signal). Thus, users can become expert in the use of the different trigger muscles proposed and choose those they find to be most convenient or best-suited to their circumstances. In the advanced version of the device comprising the object of the invention, which incorporates eyeglasses with a screen, it is also possible to view a graphic display of each EMG signal so as to facilitate users measuring and self-calibrating the their own muscular effort.

Both the details of the components not described and the specific values of the magnitudes of the myogenic languages which can be determined by the usual trial and error procedures will be evident to experts in this field.

The invention claimed is:

1. A system for remote management in ambient intelligence environments comprising:
   an interface (1) further comprising:
      an earphone or a microphone,
      at least one electromyographic signal-capturing electrode, wherein the electromyographic signal is generated by voluntary movement of a muscle or a muscle group,
      and a means for calibration, encoding and interpretation of a plurality of electromyographic signals, determining a Myogenic Language based on three parameters, the first two parameters being an amplitude (A) and a duration (D) of an electromyographic signal, the amplitude is categorized into a (AS) variable or a (AL) variable, wherein the (AL) variable represents an electromyographic signal having a larger amplitude than an amplitude of a designated electromyographic signal, and the duration is categorized into a (DS) variable or a (DL) variable, wherein the (DL) variable represents an electromyographic signal having a longer duration than the designated electromyographic signal, such that a combination of these variables is used to generate at least one myogenic four letter code including "AS/DS", "AS/DL", "AL/DS" and "AL/DL",
      the third parameter being defined as a time lapse interval between a generation of one myogenic four letter code and a next myogenic four letter code;
   a nexus module (2), an input of which is connected to the interface (1), and an output of which is a wireless transmitter-receiver;
   a controller (3) comprising means for controlling and managing a plurality of devices comprising an ambient intelligence environment, an input of the controller is wirelessly connected to the output of the nexus module (2).

2. The system for remote management in ambient intelligence environments in accordance with claim 1, wherein the interface (1) further comprises a micro-projector device capable of projecting visual messages including texts, icons or graphics, onto glasses connected to the system.

3. The system for remote management in ambient intelligence environments in accordance with claim 1, wherein the controller for controlling and managing the plurality of devices comprising the ambient intelligence environment is further comprised of PLCs, actuators and telecommunications systems.

* * * * *